Figure 1:
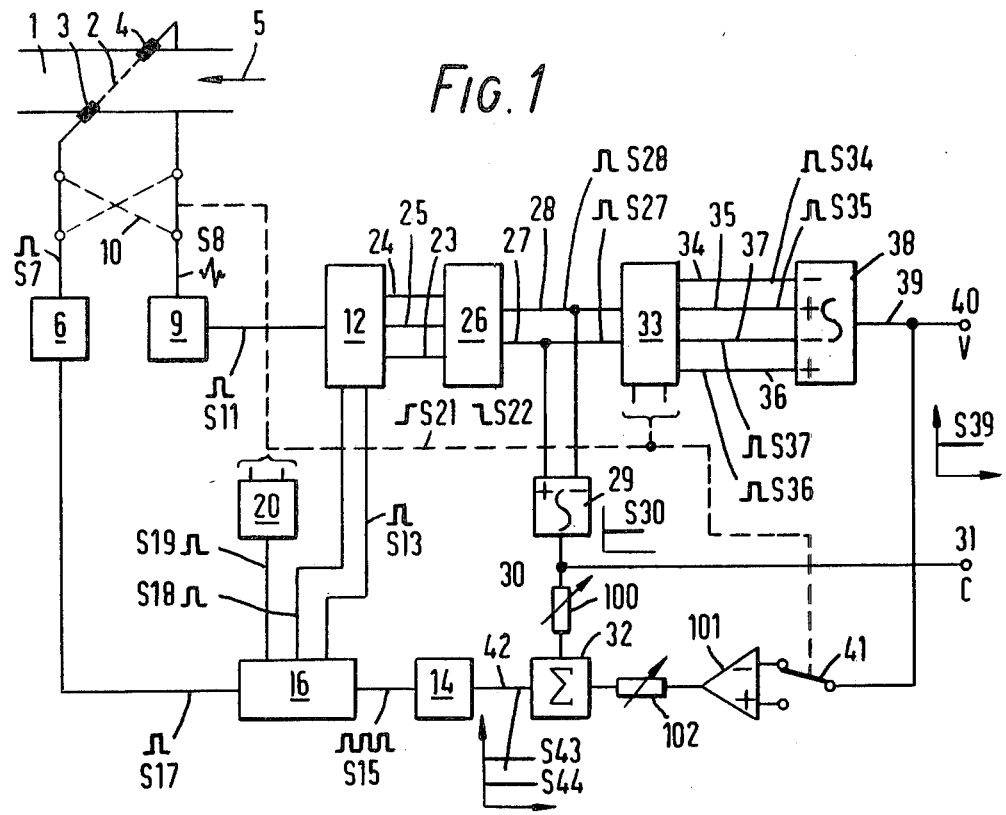

United States Patent [19]

Fick

[11] 4,114,439
[45] Sep. 19, 1978

[54] APPARATUS FOR ULTRASONICALLY MEASURING PHYSICAL PARAMETERS OF FLOWING MEDIA

[75] Inventor: Willy Julius Fick, Sonderborg, Denmark

[73] Assignee: Danfoss A/S, Nordborg, Denmark

[21] Appl. No.: 825,647

[22] Filed: Aug. 18, 1977

[30] Foreign Application Priority Data

Aug. 14, 1976 [DE] Fed. Rep. of Germany ....... 2636737

[51] Int. Cl.² .............................................. G01F 1/66
[52] U.S. Cl. ...................................... 73/194 A; 73/597
[58] Field of Search ............................. 73/597, 194 A

[56] References Cited

U.S. PATENT DOCUMENTS 3,981,191  9/1976  Brown et al. ..................... 73/194 A Primary Examiner—Charles A. Ruehl
Attorney, Agent, or Firm—Wayne B. Easton

[57] ABSTRACT

The invention relates to apparatus for ultrasonically measuring physical parameters of flowing media. A measuring path has two ultrasonic converters with transmitting and receiving devices being connected to the converters. The path has at least one component in the direction of flow and over which ultrasonic signals are sent alternately upstream and downstream. A comparator unit connected to the receiving device has an input for a reference signal from the control unit applied thereto at a predetermined time after the time of the transmitter starting signal. The comparator unit generates early or late signals when arrival signals from the receiving device come in earlier or later than the reference signal. A first signal level generator connected to said comparator unit produces a first main signal related to the velocity of sound in said media. A second signal level generator connected to the logic circuit for producing a second auxiliary signal related to the flow velocity of said media. A summating circuit has inputs connected to the first and second generators. Switch and reversing amplifier units between the summating circuit and the second signal level generator are controlled by the auxiliary flow velocity signal to and from the summating circuit to provide sum and difference outputs for the summating circuit.

4 Claims, 2 Drawing Figures

APPARATUS FOR ULTRASONICALLY MEASURING PHYSICAL PARAMETERS OF FLOWING MEDIA

The invention relates to an apparatus for ultrasonically measuring physical parameters of flowing media, particularly the speed of flow, comprising at least one measuring path which is provided with two ultrasonic converters, has at least one component in the direction of flow and over which the ultrasonic signals are alternately sent upstream and downstream, a comparator arrangement which is disposed on the receiving side, can have fed to it on the one hand arrival signals associated with the time of receipt of the ultrasonic signals and on the other hand reference signals that are delayed relatively to the time of sending, and delivers early or late signals when the arrival signals come in earlier or later than the respective reference signal, a control circuit which, in logical elements, links with the early and late signals upward and downward signals that occur in dependence on the sending direction and comprises at least two signal level generators which are controlled in dependence thereon to produce two control signals associated with the sending direction, and at least one time generator controlled by the control signals, particularly an oscillator with a downstream impulse counter, for obtaining the reference signal, wherein the output of the first signal level generator is applied to a summating circuit as the main signal and the output of the second signal level generator as the auxiliary signal and wherein a switch controlled by the sending direction and disposed in the supply line for the auxiliary signal to the summmating circuit is provided in such a way that the one control signal is formed by the sum of and the other control signal by the difference between the main signal and the auxiliary signal, and wherein the auxiliary signal is proportionally reducible upstream of or in the summating circuit.

In this apparatus, a large control loop is formed in which two frequencies f1 and f2 for the upward or downward measurement are automatically and alternately produced at the output of the time generator, these frequencies being inversely proportional to the duration of the ultrasonic signal. The auxiliary signal corresponds to the speed of flow. If it is alternately added to and subtracted from the main signal, the main signal corresponds to the sound velocity.

According to one embodiment in the older proposal, a potentiometer with which the auxiliary signal can be proportionally reduced is provided in the path of the auxiliary signal in front of the summating circuit. In this way one can work with a comparatively large auxiliary signal at the output of the associated signal level generator even at low speeds of flow. The potentiometer therefore permits a sensitivity setting such that the full control range can be utilised also at low speeds of flow. The amplifier of the summating element is followed by a second potentiometer with the aid of which the operating range of the time generator, i.e. its mean frequency, can be set. This setting is required for adaptation to the length of the measuring path because for example tubes with small diameter require a higher frequency than tubes with a larger diameter. In this case the settings of the two potentiometers influence one another so that a very accurate adaptation to local conditions calls for expert experience.

The invention is based on the problem of giving the apparatus of the aforementioned kind a construction with which the adaptation to the local conditions is considerably simplified.

This problem is solved according to the invention in that the main signal is also variable upstream of or in the summating circuit.

Since a circuit was considered in which the auxiliary signal is alternatively added to and subtracted from the main signal, the main signal has the mean value $(f_1 + f_2)/2$. The variation in the main signal upstream of or in the summating circuit therefore directly leads to a change in the mean value of the frequencies delivered by the time generator and thus to an adaptation to the length of the measuring path. By influencing the auxiliary signal, the speed of flow can be taken into account. Both adaptation settings are independent from one another because they take place in separate channels.

By reason of this independence, it is also no longer necessary to use continuously adjustable potentiometers. Instead, one can work with appropriately selected resistor stages.

It is therefore recommended that a group of selectively operable fixed resistors is applied in the path of the main signal. These fixed resistors correspond to a certain length of measuring path and can therefore be clearly associated with measuring paths which are offered by the manufacturer and which normally correspond to certain standardised tube sizes. With the aid of these resistors one can also select certain ranges for the sound velocity if different flow media are to be measured.

Similarly, one can also apply a group of selectively operable fixed resistors in the path of the auxiliary signal. These fixed resistors are then clearly associated with a respective certain maximum speed of flow.

A further simplification is obtained if the fixed resistors also form the summating resistors.

Further, the junction of the summating resistors can be connected by way of an intermediate resistor to the tapping of a potentiometer connected between two fixed potentials. This potentiometer serves to linearise the operating curves of a voltage-controlled oscillator.

In a preferred example, the group of fixed resistors in the path of the main signal and/or the group of fixed resistors in the path of the auxiliary signal are replaceable as a module. Exchange of the first-mentioned group permits, for example, the same apparatus to be used for different types of measuring path.

Further, it is recommended that the oscillator controlled by the control signals comprises a variable RC element. This permits the fundamental frequency of the oscillator to be set or switched over that by changing the resistor in the path of the main signal all local conditions can be taken into account.

Desirably, a resistor of the RC element is adjustable to enable an accurate setting to be undertaken and the condenser and/or a fixed resistor of the RC element is replaceable to permit switching over to a different frequency range.

Figure 2:
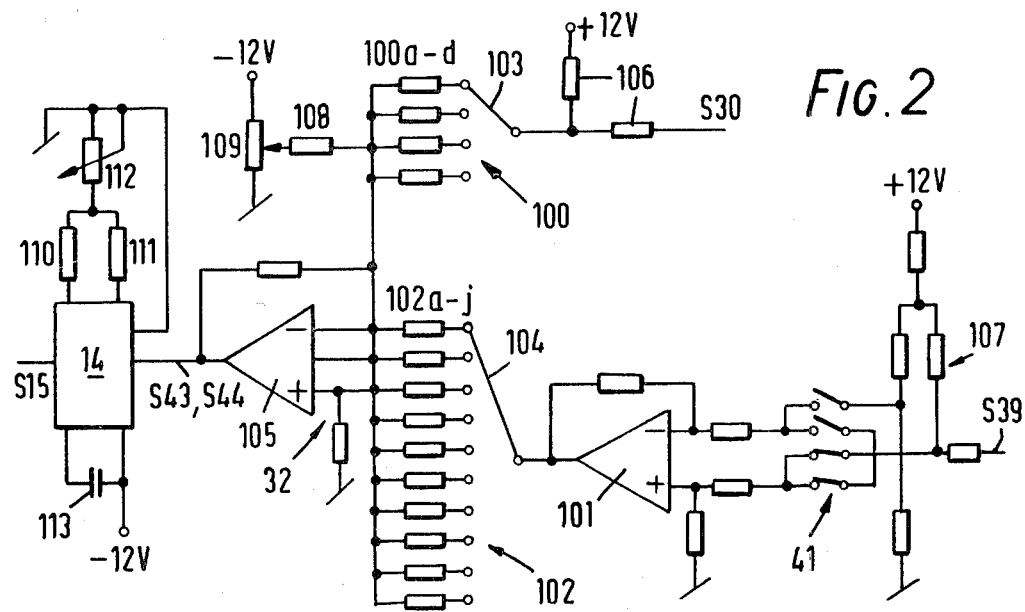

The invention will now be described in more detail with reference to an example illustrated in the drawing, wherein:

FIG. 1 is a diagrammatic circuit diagram of a measuring apparatus according to the invention, and FIG. 2 is a section of the circuit showing further details.

According to FIG. 1, an ultrasonic measuring path 2 disposed in a channel 1 is bounded by two ultrasonic converters 3 and 4 and arranged obliquely to the flow direction 5 of the medium flowing through the channel 1. A transmitting device 6 is adapted to impart to the converter 3 a D.C. impulse S7, whereupon the latter produces an ultrasonic signal which is received by the converter 4 at the end of the running time and converted to an electric signal S8 and fed to a receiving device 9. A switch 10 ensures that the converters 3 and 4 alternately serve as ultrasonic transmitter and ultrasonic receiver. A defined arrival signal S11 is derived from the signal S8 and fed to a comparator arrangement 12 and there compared with respect to time with a simultaneously supplied reference signal S13.

A voltage-controlled oscillator 14 serves as time generator of which the output oscillations are fed as an impulse series S15 to a counter 16. On commencement of counting, this counter delivers a transmission signal S17 to the transmission device 6. Upon a predetermined counter content, e.g. 256 impulses, the reference signal S13 is delivered. Between the two points of time a receiver-readiness signal S18 is delivered which prepares the comparator arrangement for the next measurement. After the measurement, the receiver-readiness signal S18 is terminated so that the receiver and comparator are made inoperative. Finally a signal S19 is fed to a bistable transmission direction generator 20 which alternately delivers downward signals S21 and upwards signals S22 which each switch the switch 10 over.

When an arrival signal S11 arrives in the comparator arrangement 12, a signal of predetermined constant amplitude and duration appears at the output 23. If the arrival signal S11 has arrived earlier than the reference signal S13, a signal is produced at the output 24. If the arrival signal arrived later, a signal occurs at the output 25. A first row 26 of logic elements links these three output signals in such a way that an early signal S27 of constant amplitude and the same duration as the signal at the output 23 occurs in a line 27 when signals are available at the two outputs 23 and 24 and a late signal S28 likewise of constant amplitude and the same duration as the signal at the output 23 occurs on a line 28 when signals are available at both outputs 23 and 25.

All early signals S27 are integrated in one direction and all late signals S28 in the opposite direction in an integrating signal level generator 29, e.g. an integrator. For the purpose of explanation, the + and − signs in the blocks 29 and 38 are to indicate the direction of integration of the early signals S27 and late signals S28. A main signal S30 in the form of a signal level variable by the early and late signals occurs at the output 30 of the signal level generator 29. This main signal S30 can be utilized directly at an output terminal 31 as a measurement for the sound velocity c. In addition, this main signal S30 is fed by way of an adjusting apparatus 100 to an input of a summating circuit 32.

The early and late signals S27 and S28 are additionally fed to a second row 33 of logic elements to which the downward and upward signals S21 and S22 are also fed. From these there are derived early upward signals S34, early downward signals S35, late upward signals S36 and late downward signals S37 at four outputs 34 – 37. The early downward signals S35 with a positive sign and the early upward signals S34 with a negative sign and possibly also the late downward signals S37 with a negative sign and the late upward signals S36 with a positive sign are fed to a second integrating signal level generator 38. Consequently there is produced at the output 39 an auxiliary signal S39 in the form of a signal level dependent on the signals S34 – S37. This auxiliary signal can be derived directly at an output terminal 40 as a measurement for the flow velocity v. In addition, the auxiliary signal is fed by way of a switch 41, a reversing amplifier 101 as well as an adjusting apparatus 102 with alternately positive and negative value to the second input of the summating circuit 32. The switch 41 is switched over in dependence on the downward and upward signals S21 and S22. Consequently control signals S43 and S44 alternately occur at the output 42 of the summating circuit and respectively correspond to the sum of or difference between the main signal S30 and the main signal S39. These control signals control the voltage-controlled oscillator 14 in such a way that the impulse row S15 alternately has a larger frequency f1 associated with the downward measurement and a smaller frequency f2 associated with the upward measurement. By altering the adjusting apparatus 100, the main signal S30 is changed. This leads to a change in the mean frequency of the oscillator 14. If instead of the illustrated tube 1 use is made of a tube of smaller diameter and thus a shorter measuring path 2, the adjusting apparatus 100 can be altered so that the mean frequency is increased and account is taken of the shorter running time of the ultrasonic signal.

By altering the adjusting apparatus 102, one can set the sensitivity of measuring the speed of flow. A more intense proportional reduction of the auxiliary signal S39 by the adjusting apparatus 102 results in the operating range of the integrator 38 being fully utilized even with a relatively small speed of flow.

The two settings at the adjusting apparatuses 100 and 102 are independent from one another because they are undertaken in different channels.

FIG. 2 shows that the adjusting apparatus 100 consists of a group of four fixed resistors 100a – d which are made operative by a reversing switch 103 whilst the adjusting apparatus 102 consists of a group of ten fixed resistors 102a – j which can be made operative by a reversing switch 104. Whichever fixed resistor happens to be operative also forms a summating resistor of the summating circuit 32 which also comprises a summating amplifier 105. The main signal S30 is fed to the adjusting apparatus 100 by way of a resistor arrangement 106 and the auxiliary signal S39 is fed to the adjusting apparatus 102, possibly after a pretreatment, by way of a resistor arrangement 107 to the switch 41 in the form of an electronic double reversing switch and to the amplifier 101 which transmits the signal with a positive or negative sign depending on the switch position.

The inverting input of the summating amplifier 105 is applied by way of a preliminary resistor 108 to the tapping of a potentiometer 109 because it is fed by a fixed voltage. The characteristic curve of the oscillator 14 can be linearized with the aid of this potentiometer.

The oscillator 14 comprises an RC element which comprises the two fixed resistors 110 and 111, the variable resistor 112 and the condenser 113. By replacing the condenser 113, the fundamental frequency of the oscillator 14 can be changed in large steps. The desired fundamental frequency can then be accurately set with the aid of the adjusting resistor 112.

When the apparatus has been delivered and connected to a measuring path, the reversing switch 103 need merely be switched to that resistor 100a – d which is associated with the measuring path in question. The reversing switch 104 is then connected to that fixed resistor 102a – j associated with that maximum flow velocity from which the best readings are expected. If for example there is a maximum flow velocity of 4.7 m/s, that resistor is selected which is associated with the next higher maximum flow velocity, e.g. 5 m/s. The resistors can also be associated with different ranges of the sound velocity, e.g. between 1200 and 1800 m/s.

Since every manufacturer supplies only a predetermined number of measuring positions which are generally associated with certain standard tube sizes, it is not difficult to associate the group of fixed resistors 100a – d to these measuring paths. These fixed resistors can also be in the form of a replaceable module, for example to permit adaptation to a different type of measuring location or a different range of sizes of measuring locations. Similarly, an adaptation in surges can also take place by replacing the condenser 113.

It is clear that instead of the illustrated individual connection of fixed resistors one can also use a resistor chain with a plurality of tappings to which the reversing switch 103 or 104 can be applied.

I claim:

1. Apparatus for ultrasonically measuring physical parameters of flowing media, comprising, a measuring path provided with two ultrasonic converters, transmitting and receiving devices connected to said converters, said path having at least one component in the direction of flow and over which ultrasonic signals are sent alternately upstream and downstream, control means for applying a starting signal to said transmitting device, switch means operated by said control means for alternately connecting said transmitter and receiver to opposite ones of said converters, comparator means connected to said receiving device and having an input for a reference signal from said control means applied thereto at a predetermined time after the time of said transmitter starting signal, said comparator means generating early or late signals when arrival signals from said receiving device come in earlier or later than said reference signal, a first signal level generator connected to said comparator means for producing a first main signal related to the velocity of sound in said media, a logic circuit connected to said comparator means and said control means, a second signal level generator connected to said logic circuit for producing a second auxiliary signal related to the flow velocity of said media, a summating circuit having inputs connected to said first and second generators, a time generator having an input connected to said summating circuit and an output connected to said control means, switch and reversing amplifier means between said summating circuit and said second signal level generator controlled by said control means for alternately adding and subtracting said auxiliary flow velocity signal to and from said summating circuit to provide sum and difference outputs for said summating circuit, first variable resistor means between said summating circuit and said first signal generator for adjustably varying said main signal, and second variable resistor means between said summating circuit and said second signal generator for varying said auxiliary signal.

2. Apparatus according to claim 1 wherein at least one of said variable resistor means includes a group of selectively operable fixed resistors.

3. Apparatus according to claim 1 wherein said first variable resistor means includes a group of selectively operable fixed resistors, a potentiometer between two fixed potentials, said potentiometer being connected to the junction between said group fo resistors and said summating circuit.

4. Apparatus according to claim 1 wherein said time generator includes a variable RC combination.

* * * * *